(12) United States Patent
Dallara et al.

(10) Patent No.: US 7,122,051 B1
(45) Date of Patent: Oct. 17, 2006

(54) UNIVERSAL LENGTH SIZING AND DOCK FOR MODULAR BIFURCATED ENDOVASCULAR GRAFT

(75) Inventors: Mark Dallara, Tampa, FL (US); John Pazienza, Pompano Beach, FL (US); Bennie Gladdish, Davie, FL (US); Alfred Concemi, Flagstaff, AZ (US)

(73) Assignee: Endovascular Technologies, Inc., Santa Clara, CA (US)

( * ) Notice: Subject to any disclaimer, the term of this patent is extended or adjusted under 35 U.S.C. 154(b) by 297 days.

(21) Appl. No.: 10/194,426

(22) Filed: Jul. 12, 2002
(Under 37 CFR 1.47)

(51) Int. Cl.
*A61F 2/06* (2006.01)
(52) U.S. Cl. .................... 623/1.35; 623/1.15
(58) Field of Classification Search ............ 623/1.35, 623/1.15
See application file for complete search history.

(56) References Cited

U.S. PATENT DOCUMENTS

| | | |
|---|---|---|
| 3,657,744 A | 4/1972 | Ersek |
| 4,140,126 A | 2/1979 | Choudhury |
| 4,562,596 A | 1/1986 | Kornberg |
| 4,787,899 A | 11/1988 | Lazarus |
| 5,064,435 A | 11/1991 | Porter |
| 5,489,295 A | 2/1996 | Piplani et al. |
| 5,562,724 A | 10/1996 | Vorwerk et al. |
| 5,575,817 A | 11/1996 | Martin |
| 5,609,627 A | 3/1997 | Goicoechea et al. |
| 5,628,788 A | 5/1997 | Pinchuk |
| 5,632,772 A | 5/1997 | Alcime et al. |
| 5,639,278 A | 6/1997 | Dereume et al. |
| 5,653,743 A | 8/1997 | Martin |
| 5,676,696 A | 10/1997 | Marcade |
| 5,683,449 A | 11/1997 | Marcade |
| 5,683,450 A | 11/1997 | Goicoechea et al. |
| 5,716,365 A | 2/1998 | Goicoechea et al. |
| 5,718,724 A | 2/1998 | Goicoechea et al. |
| 5,723,004 A | 3/1998 | Dereume et al. |
| 5,741,325 A | 4/1998 | Chaikof et al. |
| 5,755,769 A | 5/1998 | Richard et al. |
| 5,776,180 A | 7/1998 | Goicoechea et al. |
| 5,800,508 A | 9/1998 | Goicoechea et al. |
| 5,824,037 A | 10/1998 | Fogarty et al. |
| 5,824,042 A | 10/1998 | Lombardi et al. |
| 5,855,598 A | 1/1999 | Pinchuk |

(Continued)

FOREIGN PATENT DOCUMENTS

DE 9319267 4/1994

(Continued)

OTHER PUBLICATIONS

Chuter, et al., "Transfemoral Endovascular Aortic Graft Placement," Journal of Vascular Surgery, vol. 18, No. 2, Aug. 1993, pp. 185-197.

(Continued)

*Primary Examiner*—Thomas C. Barrett
(74) *Attorney, Agent, or Firm*—Fulwider Patton Lee & Utecht, LLP (57) ABSTRACT

A bifurcated graft having a trunk portion and two limb portions, each defined by a docking end and a non-docking end, that is assembled in-situ. The trunk and limb portions are supported by a combination of full and partial stent structures that are connected by longitudinal stent struts to form a continuous stent lattice. The diameters of the docking sections may be standardized such that any limb portion may be inserted into any trunk portion, providing the same degree of mechanical interference for trunk and limb portions having non-docking ends of various diameters.

37 Claims, 8 Drawing Sheets

U.S. PATENT DOCUMENTS

| | | | |
|---|---|---|---|
| 5,916,263 | A | 6/1999 | Goicoechea et al. |
| 5,938,696 | A | 8/1999 | Goicoechea et al. |
| 5,993,481 | A | 11/1999 | Marcade et al. |
| 6,015,431 | A | 1/2000 | Thornton et al. |
| 6,051,020 | A | 4/2000 | Goicoechea et al. |
| 6,099,558 | A | 8/2000 | White et al. |
| 6,102,938 | A | 8/2000 | Evans et al. |
| 6,117,167 | A | 9/2000 | Goicoechea et al. |
| 6,123,722 | A | 9/2000 | Fogarty et al. |
| 6,149,682 | A | 11/2000 | Frid |
| 6,165,213 | A | 12/2000 | Goicoechea et al. |
| 6,302,906 | B1 | 10/2001 | Goicoechea et al. |
| 2002/0019659 | A1 | 2/2002 | Goicoechea et al. |

FOREIGN PATENT DOCUMENTS

| | | |
|---|---|---|
| FR | 2 678 508 | 1/1993 |
| SU | 660689 | 5/1979 |
| SU | 1217402 | 3/1986 |
| SU | 1457921 | 2/1989 |

OTHER PUBLICATIONS

Parodi et al., "Transfemoral Intraluminal, Graft Implantation for Abdominal Aortic Aneurysms," Annals of Vascular Surgery, vol. 5, No. 6, 1991, pp. 491-499.

Criado et al., "Transluminal Recanalization, Angioplasty and Stenting in Endovascular Surgery: Techniques and Applications," From Greenhalgh, Vascular and Endovascular Surgical Techniques, 3rd Edition, 1994, pp. 49-70.

Marin et al., "Endoluminal Stented Graft Aorto-Bifemoral Reconstruction," from Greenhalgh, Vascular and Endovascular Surgical Techniques, 3.sup.rd Edition, 1994, pp. 100-104.

May et al., "Transuluminal Placement of a Prosthetic Graft-Stent Device for Treatment of Subclavian Artery Aneurysm," Journal of Vascular Surgery, vol. 18, No. 6, Dec. 1993, pp. 1056-1059.

Chuter, T., "Bifurcated Endovascular Graft Insertion for Abdominal Aortic Aneurysm," from Greenhalgh, Vascular and Endovascular Surgical Techniques, 3.sup.rd Edition, 1994, pp. 92-99.

Moore, W.S., "Transfemoral Endovascular Repair of Abdominal Aortic Aneurysm Using the Endovascular Graft System Device," from Greenhalgh, Vascular and Endovascular Surgical Techniques, 3.sup.rd Edition, 1994, pp. 78-91.

UNIVERSAL LENGTH SIZING AND DOCK FOR MODULAR BIFURCATED ENDOVASCULAR GRAFT

BACKGROUND OF THE INVENTION

This invention relates to intraluminal grafts for repairing defects in arteries and other lumens within the body. More particularly, the present invention relates to modular systems for forming endovascular grafts for implantation and assembly in-situ for repairing defective body lumens.

An abdominal aortic aneurysm is a sac caused by an abnormal dilation of the wall of the aorta as it passes through the abdomen. The aorta is the main artery of the body, supplying blood to various organs and parts of the body. It arises from the left ventricle of the heart, passes upward, bends over and passes down through the thorax and through the abdomen, and finally divides into the two iliac arteries which supply blood to the pelvis and lower extremities. The aneurysm ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is removed and replaced with a prosthetic device, such as a synthetic graft.

As with all major surgeries, there are many disadvantages to the foregoing surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the loss of the existing thrombosis to support and reinforce the graft; the unsuitability of the surgery for many patients, particularly older patients exhibiting co-morbid conditions; and the problems associated with performing the surgical procedure on an emergency basis after the aneurysm has already ruptured.

In view of the foregoing disadvantages of conventional surgical repair techniques, techniques have been developed for repairing abdominal aortic aneurysms by intraluminally delivering an aortic graft to the aneurysm site through the use of a catheter based delivery system, and securing the graft within the aorta using an expandable stent. Since the first documented clinical application of this technique, the technique has gained more widespread recognition and is being used more commonly. As vascular surgeons have become more experienced with this endovascular technique, however, certain problems have been encountered.

One problem has been the difficult nature of the procedure. Another problem has been the kinking and/or twisting of the graft both during and after the graft has been implanted. Still other problems relate to the need for accurate preoperative measurements to be made on the morphology of the aneurysm and the surrounding arterial structure, including the length of the aneurysm, the infrarenal aortic length and diameter, the length and diameter of the aorta between the aneurysm and the iliacs, the diameter of the iliacs, and the angle between the iliacs and the aorta. The difficulty in making these measurements accurately and the wide variations in these measurements among patients mandates that the bifurcated grafts be available in a wide range of sizes and configurations.

Endovascular repair of the abdominal aortic aneurysm (AAA) using a stent/graft prosthesis that is assembled in-situ is gaining acceptance due to reduced surgical complications, and providing an alternative solution for patients that cannot be treated surgically. However, the large degree of variation in the geometry and dimensions of vascular anatomy from patient to patient poses a problem for the physician in selecting a device, and for the manufacturer in the number of parts required in inventory.

Current modular bifurcated systems are often designed to specific trunk-to-limb diameter ratios (e.g. a stent with a 24 mm trunk will have 12 mm limbs) and most designs have one or both limb(s) pre-attached to the trunk. Also, current modular bifurcated stents are often designed with a limited amount of adjustability in length. If a two-piece system already has one limb attached to the trunk, there is a fixed length for one side of the device. Furthermore, the contralateral limb (or each limb in a three-piece device) typically has a narrow insertion range. These approaches limit the choices that a physician has in selecting a device for a given patient, and potentially excludes patients with abnormal vasculature.

Therefore, there exists a need for a bifurcated graft and an implantation method which will overcome the foregoing deficiencies of the prior art. More particularly, there exists a need for a modular graft system which will more accurately accommodate the widely varying arterial sizes in patients, as well as the other size considerations now faced by the surgeon. The present invention addresses these and other needs.

SUMMARY OF THE INVENTION

Briefly and in general terms, the present invention is embodied in a graft device that is assembled in-situ. The graft device includes a docking station providing a relatively broad insertion range.

In one aspect, a bifurcated endovascular graft having a trunk portion and two limb portions is provided, each defined by a docking end and a non-docking end. The graft will have the ability to be delivered endovascularly to repair an abdominal aortic aneurysm (AAA) and assembled in-situ by inserting the docking section of each limb portion into one of two docking sections of the trunk portion. The mechanical seal between each limb portion and the trunk portion is effectuated by undersizing each of the trunk portion docking sections relative to the corresponding limb docking sections.

In another aspect, the trunk portion and each limb portion are not supported by a full stent structure. Rather, each portion is supported by a full stent structure at the non-docking end, a full or partial stent structure at the docking end, and a partial stent structure between them. The full stent structure at the non-docking end of the trunk portion and each limb portion allows each portion to be fully sealed within the lumen. The partial or full stent structure at the docking end of the trunk portion and each limb portion provides a variable length docking section which can accommodate various trunk and limb portions having a standardized diameter. The partial stent structure between the non-docking and docking ends of each portion facilitates economical manufacturing while providing axial and longitudinal support without reducing flexibility.

In yet another aspect, the docking sections of the trunk portion allow each limb portion to be inserted by a varying distance, thereby providing adjustability for the total length of the device with respect to each iliac artery. The physician has the flexibility to adjust the length of the device for each iliac artery over a relatively wide range. This allows the physician to accommodate a larger percentage of patients, some of whom might be excluded from treatment with another device, as well as facilitating variable relative limb portion lengths without having to provide limb portions of different lengths.

In yet a further aspect, the diameter of the docking sections are standardized such that any size limb portion may be inserted into any size trunk portion, providing the same degree of mechanical interference for trunk and limb portions having non-docking ends of various diameters. The docking section of all limbs can be of the same nominal diameter, specifically designed to fit within the trunk portion docking sections, which will be undersized the same amount relative to the limb docking sections for all trunk portions. Therefore, the seal joint will be identical for any trunk portion/limb portion combination, regardless of the relative diameters of the aorta and the iliac arteries. The physician can use any combination of limb portions with any trunk portion, providing maximum flexibility to treat a wide range of sizes and allowing the physician to select a stent-graft that is optimized to the patient's anatomy.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENTS

As shown in the exemplary drawings and for purposes of illustration, the invention is embodied in a prosthetic bifurcated graft implant that is assembled in-situ from a trunk portion having at least one distal docking section and at least one limb portion having a proximal docking section, the trunk and limb portions supported by a stent structure that consists of full stent rings and partial stent rings connected by stent struts.

Figure 1:
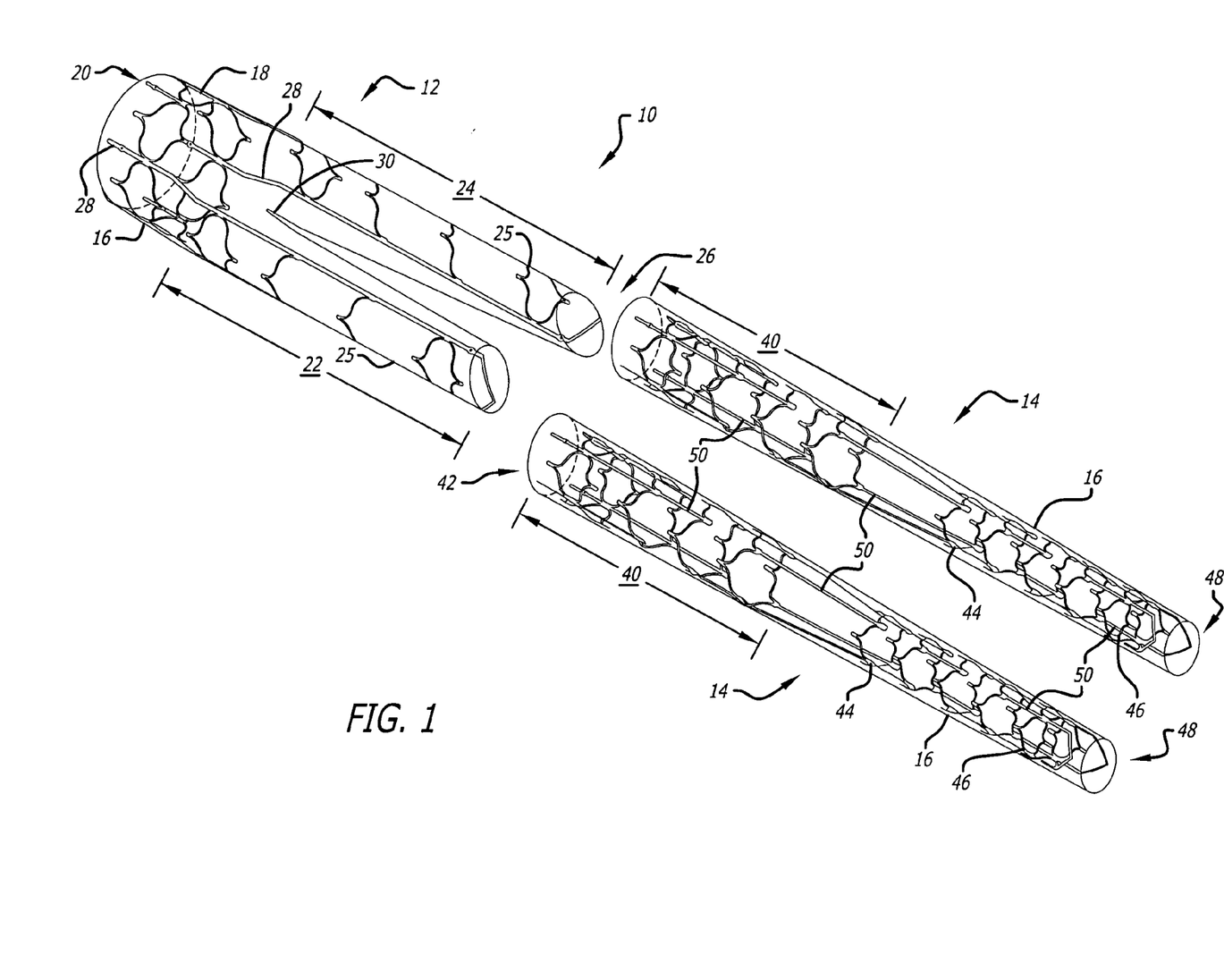
FIG. 1 is a partial perspective view of a bifurcated stent-graft of the present invention.

Referring to FIG. 1, a bifurcated graft 10 is shown. It has a trunk portion 12 and two limb portions 14. Each portion is covered by graft material 16.

The trunk portion 12 has a stent structure with a sealing ring 18 at the proximal end 20, an ipsi-lateral docking section 22 and a contra-lateral docking section 24 at the distal end 26, and longitudinal stent struts 28 which support the sealing ring 18 and docking sections 22, 24. In an alternate embodiment, it is also contemplated that the trunk portion can include a single or at least one longitudinal strut. The ipsi-lateral docking section 22 and contra-lateral docking section 24 provide an area of overlap between the trunk portion 12 and limb portions 14, the area of overlap being variable such that the bifurcated graft 10 has a variable overall length without having to manufacture a new stent lattice. The graft material 16 forms a crotch 30 between the docking sections 22, 24 to thereby define a pair of leg portions 25. The stent structure formed by the sealing rings 18, docking sections 22, 24, and longitudinal stent struts 28 provides a continuous stent lattice that extends longitudinally from the proximal end 20 to the distal end 26.

Each limb portion 14 has stent structure with a docking section 40 at the proximal end 42, support rings 44, a sealing ring 46 at the distal end 48, and longitudinal stent struts 50 which support the docking section 40, support rings 44 and sealing rings 46. The limb portion 14 docking section 40 mates with the trunk portion 12 docking section 22, 24 to facilitate the variable length bifurcated graft 10. The stent structure formed by the docking section 40, support rings 44, and sealing ring 46, and longitudinal stent struts 50 provides a continuous stent lattice that extends longitudinally from the proximal end 42 to the distal end 48.

The support struts 28, 50 of the trunk portion 12 and limb portions 14, respectively, provide support in areas where the stent structure either contains no stent cells or stent cells which do not traverse the entire 360° circumference of the stent-graft. The stent structures of the trunk portion 12 and limb portions 14, therefore, provide sufficient radial stiffness to resist kinking of the graft material and longitudinal stiffness to ease retraction of the delivery catheter without reducing the flexibility of the assembled graft implant while still allowing the trunk portion 12 and limb portions 14 to be sufficiently packed for delivery to the implant site.

It is contemplated that the trunk portion 12 may be packed to an 18F OD and each limb portion 14 may be packed to a 14F OD. It is further contemplated that the assembled graft will be sufficiently flexible to accommodate a 60° bend in the aorta without significant reduction in flow. The stent structures of the trunk portion 12 and limb portions 14 can be made from Nitinol and are self-expanding upon deployment from a delivery catheter. Other materials such as Elgiloy® and other balloon expandable structures are also contemplated. Moreover, although the drawings depict a particular stent configuration, various other embodiments can also be employed.

The graft 10 is assembled in vivo by implanting the trunk portion 12 and then implanting each limb portion 14 such that the limb portion docking section 40 engages one of the trunk portion docking sections 22, 24. Methods known in the art of endovascular implants are used to deliver the trunk portion 12 and each limb portion 14.

Referring to FIGS. 2A through 2D, the variable docking sections 22, 24, 40 of the trunk portion 12 and limb portions 14, respectively, allow a physician to vary the relative length of each limb portion 14 of the stent-graft 10 as it is assembled in-situ. By varying the amount by which a limb portion 14 docking section 40 is inserted axially into a trunk portion 12 docking section 22, 24, the relative length of the limb portion 14 may be varied between two extremes; a minimum and maximum length based upon maximal and minimal insertion.

Figure 2A:
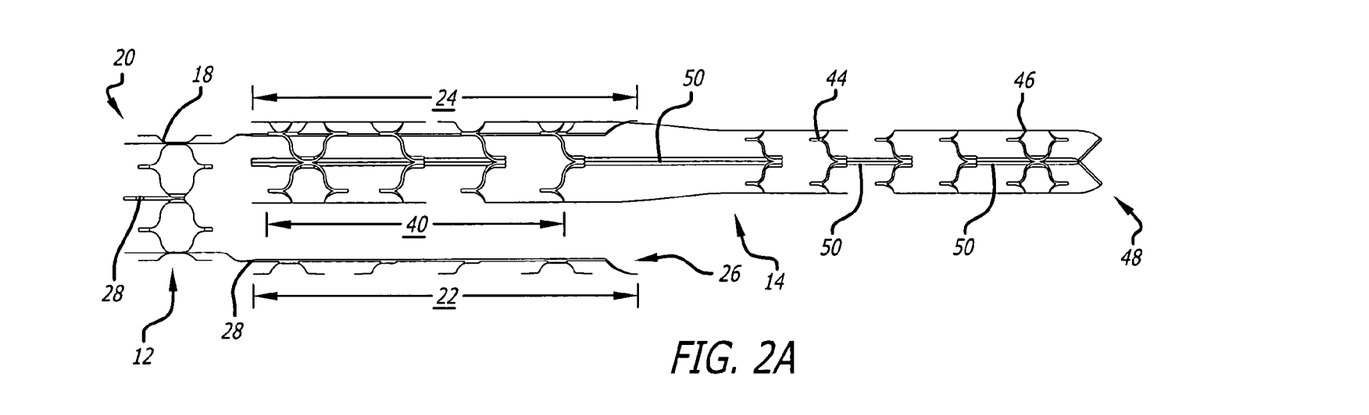
FIG. 2A is a partial cross-sectional view of a bifurcated graft of the present invention with one limb inserted and the docking sections maximally engaged for minimum device length.
Figures 2B, 2D:
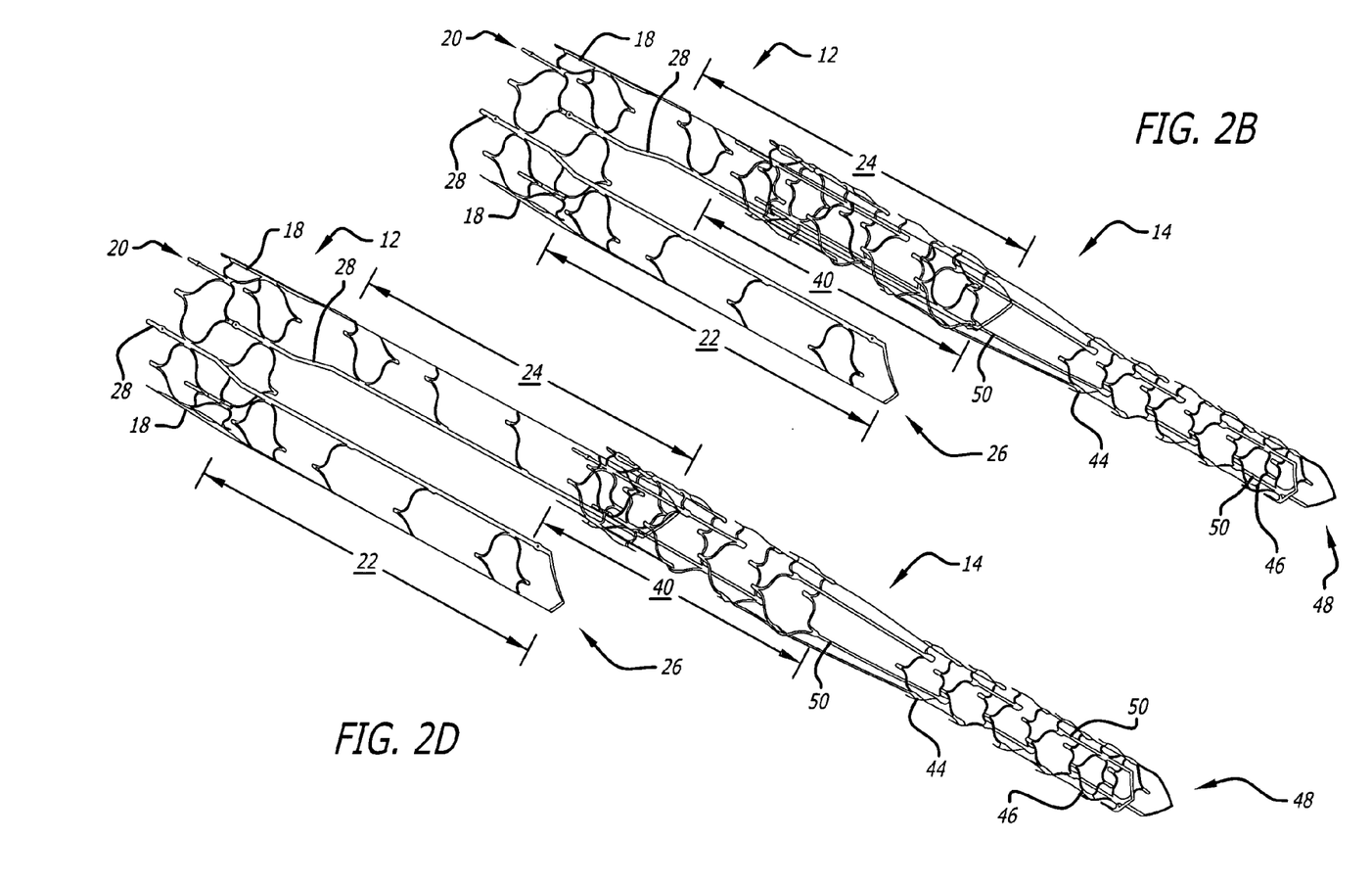
FIG. 2B is a partial cross-sectional view of the bifurcated graft shown in FIG. 2A.
FIG. 2D is a partial cross-sectional view of the bifurcated graft shown in FIG. 2C.
Figure 2C:
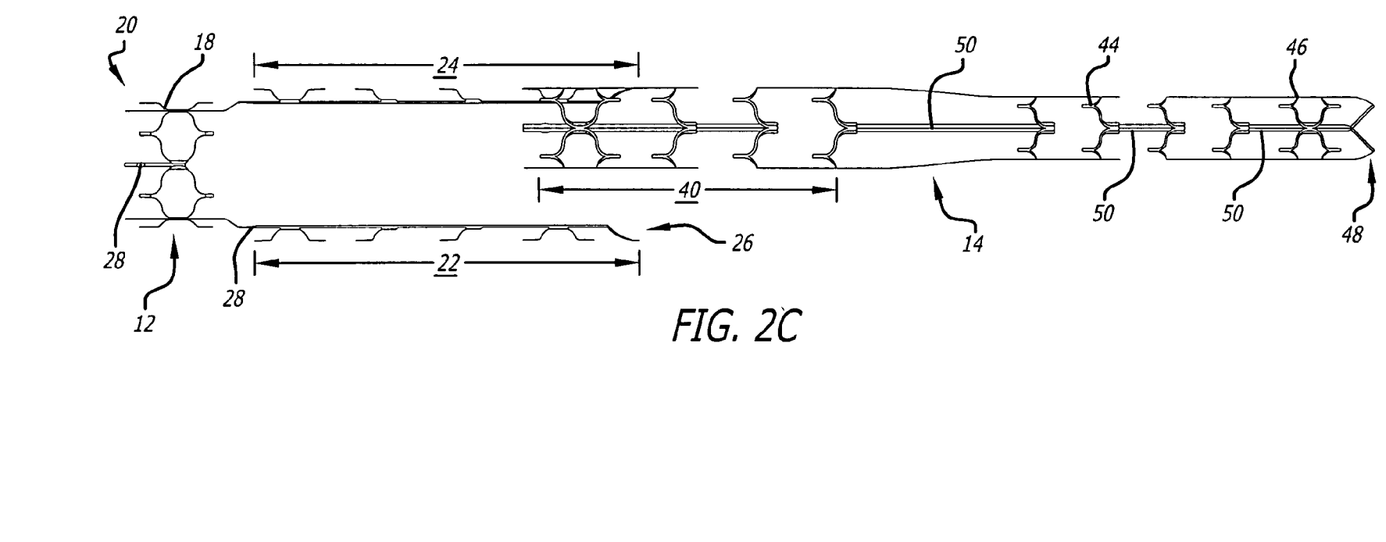
FIG. 2C is a partial cross-sectional view of a bifurcated graft of the present invention with one limb inserted and the docking sections minimally engaged for maximum device length.

FIGS. 2A and 2B show a limb portion 14 docking section 40 inserted the maximal amount into the trunk portion 12 ipsi-lateral docking section 24, thereby forming a limb portion 14 with the minimum allowable length. FIGS. 2C and 2D show a limb portion 14 docking section 40 inserted a relatively minimal amount into the trunk portion 12 ipsi-lateral docking section 24, thereby forming a limb portion 14 with the maximum allowable length.

It is contemplated that the variable docking sections 22, 24, 40 of the trunk portion 12 and limb portions 14, respectively, will facilitate a variation of up to 60 millimeters in the overall length of the assembled stent-graft 10, from the proximal end 20 of the trunk portion 12 to the distal end 48 of a limb portion 14. The present invention forms circumferential contact between the outer surface of the limb portion 14 and the inner surface of the trunk portion 12 all along the respective overlapping docking sections 22, 24, 40 to provide a superior seal. In contrast, prior art devices only have overlapping circumferential contact between 10 to 20 millimeters. The minimum overlap between the docking sections 22, 24, 40 of the trunk portion 12 and limb portions 14, respectively, is contemplated to be at least 10 and preferably 20 millimeters. All limb portions 14 are contemplated to be the same length appropriately sized for the desired overall variable length.

The stent structure of the trunk portion 12 can contain at least one sealing ring 18 extending 360° around the circumference of the proximal end 20. In one embodiment, the stent structure has an even number of full cells to facilitate packing and deployment. However, a stent structure with an odd number of full cells is also contemplated. Additional sealing rings 18 may be provided.

The docking sections 22, 24 of the trunk portion 12 may additionally contain any combination of full, half, or quarter cells extending longitudinally at the distal end 26 of the trunk portion 12 and from 60° to 360° around the circumference.

Moreover, it is contemplated that the trunk portion 12 contain at least two longitudinal stent struts 28 to support the sealing stents 18 and docking sections 22, thereby providing a continuous stent lattice. Additional longitudinal stent struts 28 may be provided.

Figure 3:
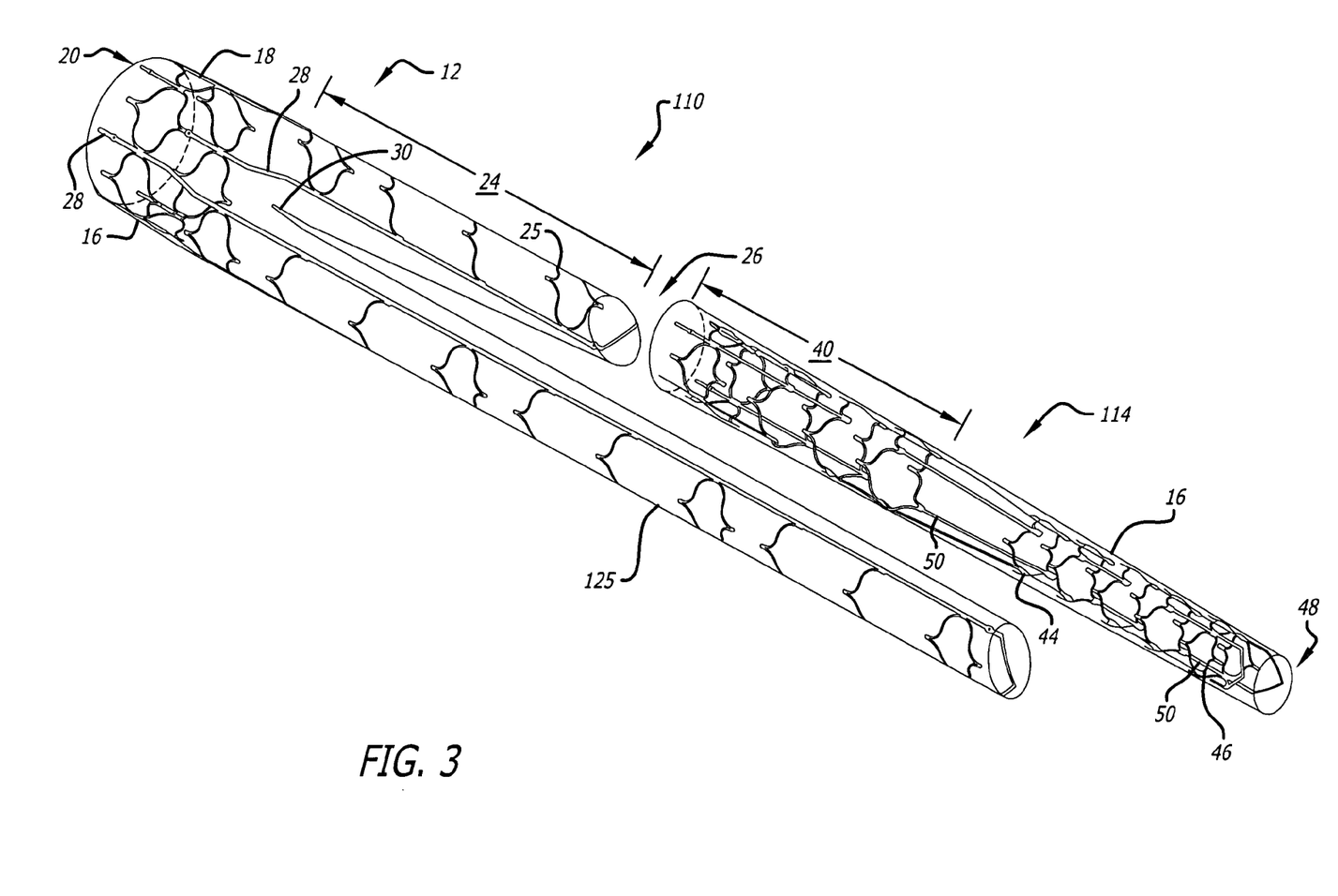
FIG. 3 is a partial perspective view of an alternate embodiment of the bifurcated stent-graft shown in FIG. 1.

Although the bifurcated graft 10 illustrated in FIG. 1 has a trunk portion 12 with variable ipsi-lateral 22 and contra-lateral 24 docking sections, it is contemplated that a bifurcated graft may be provided with one fixed leg portion and one variable length leg portion. Referring to FIG. 3, a bifurcated graft 110 is shown with a stent structure having a variable contra-lateral docking section 24 and a fixed-length ipsi-lateral leg portion 125. A single limb portion 114 is inserted into the contra-lateral docking section 24 to form a bifurcated graft 110 having a variable overall length on the contra-lateral side.

Figure 4:
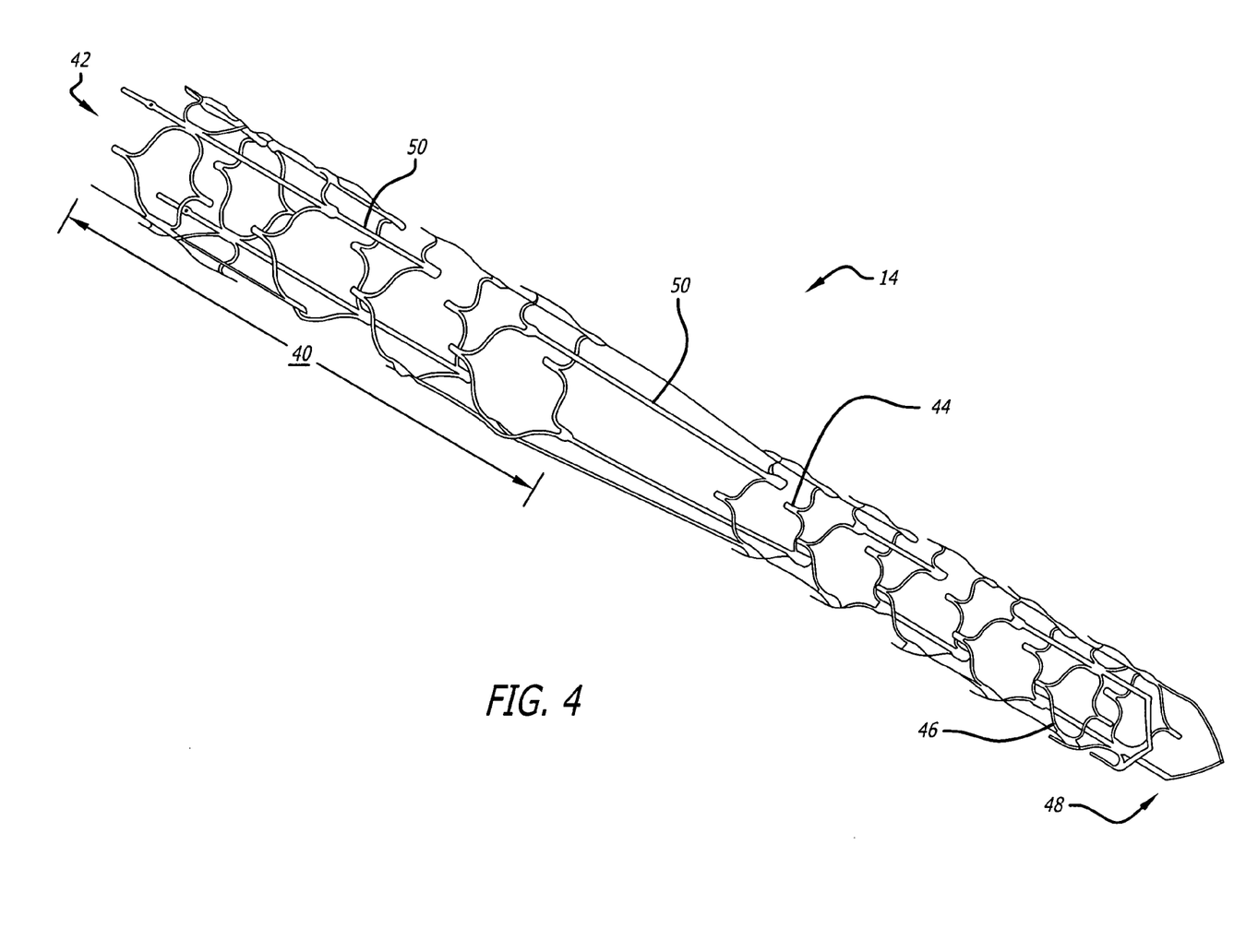
FIG. 4 is a perspective view of a limb portion stent structure of the present invention.

Referring to FIG. 4, the stent structure of a limb portion 14 of the invention is shown. The docking section 40 has a single row of full cells and additional rows of half cells extending 360° around the circumference of the proximal end 42. Additional support rings 44, having rows of half cells extending 360° around the circumference, are located distal the docking section 40. A sealing ring 46, having a single row of full cells, extends 360° around the circumference, of the distal end 48. Multiple longitudinal stent struts 50 support the docking section 40, support rings 44 and sealing ring 46, thereby providing a continuous stent lattice.

The docking section 40 of each limb portion 14 contains at least one row of full cells extending 360° around the circumference of the proximal end 42 and, in one embodiment, has an even number of cells although an odd number of cells is also contemplated. Additional rows of full, half or quarter cells extending longitudinally at the proximal end 42 and from 60° to 360° around the circumference may be provided. Moreover it is contemplated that one or more rows of support rings 44 may be provided distal the docking section 40, each having rows of full, half or quarter cells and extending from 60° to 360° around the circumference.

The stent structure of the limb portions 14 can contain at least one sealing ring 46 of full cells extending 360° around the circumference of the distal end 48 and, in one embodiment, has a number of cells selected to facilitate packing and deployment. Additional sealing rings 46 having rows of full, half or quarter cells and extending from 60° to 360° around the circumference of the distal end 48 may be provided.

Moreover, it is contemplated that each limb portion 14 contain at least one longitudinal stent strut 50 to support the docking section 40, support rings 44, and sealing stents 46, thereby providing a continuous stent lattice. Additional longitudinal stent struts 50 may be provided.

Figure 5:
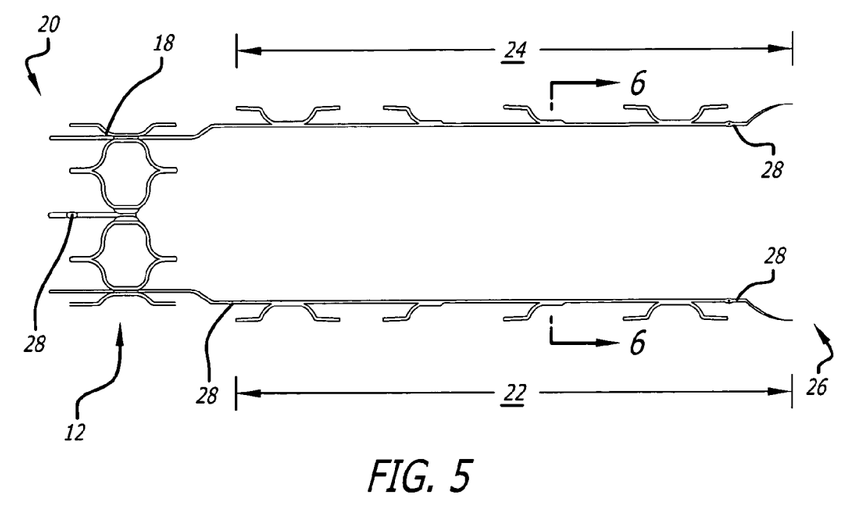
FIG. 5 is a perspective view of an embodiment of a trunk portion stent structure of the present invention having docking sections which are supported on only one side.
Figures 6A, 6B:
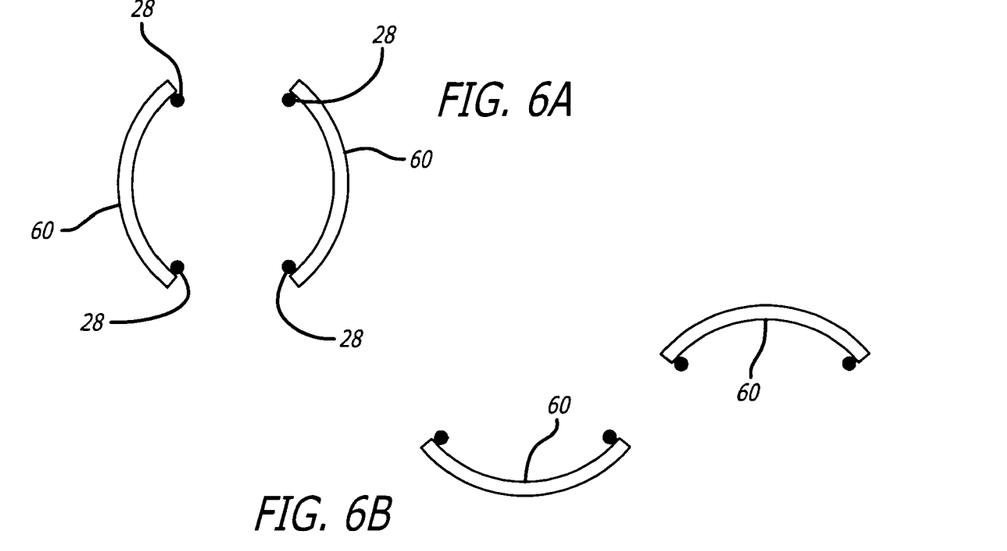
FIG. 6A is a schematic, cross-sectional view of the trunk portion shown in FIG. 4 across line 6—6 with overlapping docking sections.
FIG. 6B is a schematic, cross-sectional view of a trunk portion depicting non-overlapping docking sections.

As best seen in FIGS. 5 and 6A, the trunk portion 12 can embody docking sections 22, 24 that provide support less than an entire circumference of a leg of the device. In FIG. 6A, item 60 schematically represents the area of support provided by the docking sections 22, 24. The graft material (not shown) covering the trunk portion 12 docking sections 22, 24 is undersized relative to the limb portion docking section 40 such that, when a limb portion 14 is deployed within one of the docking sections 22, 24, the stent structure of the limb portion 14 docking section 40 cannot deploy to its full diameter (For reference, See FIG. 1). Therefore, the mechanical seal between the trunk portion 12 and a limb portion 14 is effectuated by the limb portion 14 docking section 40 being constrained from deploying to its full diameter by the combination of the trunk portion 12 docking section 22, 24 stent structure on one side and the graft material between the crotch and the distal end of the trunk portion 12 on the other side.

Figure 7:
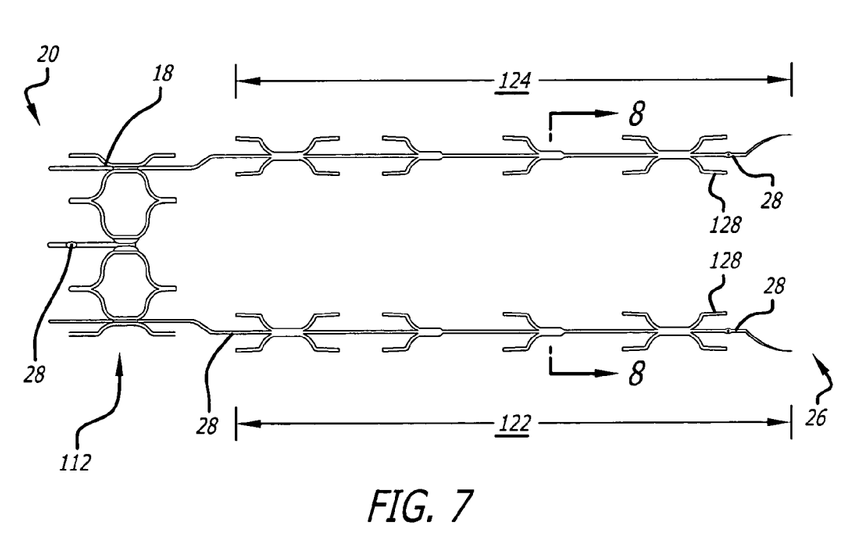
FIG. 7 is a perspective view of an embodiment of a trunk portion stent structure of the present invention having docking sections which are supported on both sides.
Figure 8A:
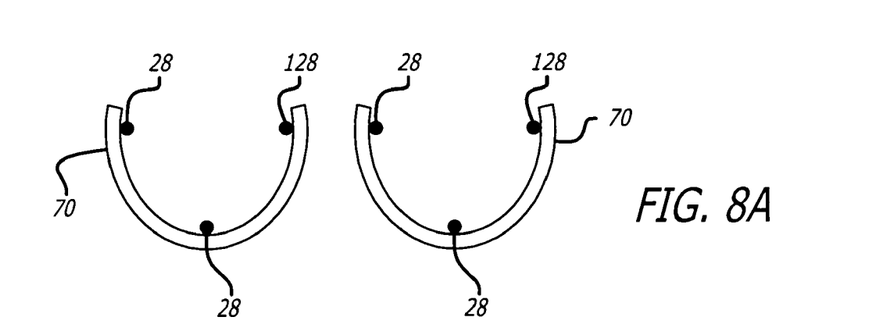
FIG. 8A is a schematic, cross-sectional view of the trunk portion shown in FIG. 6 across line 8—8 with overlapping docking sections.

In another embodiment of the invention, the trunk portion 112 has docking sections 122, 124 with an additional longitudinal stent strut 128 and attached ring structure, as shown in FIGS. 7 and 8A. In FIG. 8A, item 70 schematically represents the area of support provided by the docking sections 122, 124. The docking sections 122, 124 are supported on both sides by the stent structure. As before, each trunk portion 12 docking section 122, 124 is undersized relative to the limb portion docking section 40 so that when a limb portion 14 is deployed within one of the docking sections 122, 124, the mechanical seal between the trunk portion 112 and a limb portion 14 is effectuated by the limb portion 14 docking section 40 being constrained from deploying to its full diameter by both the undersized graft material (not shown) and the trunk portion 112 docking sections 122, 124.

Figure 8B:
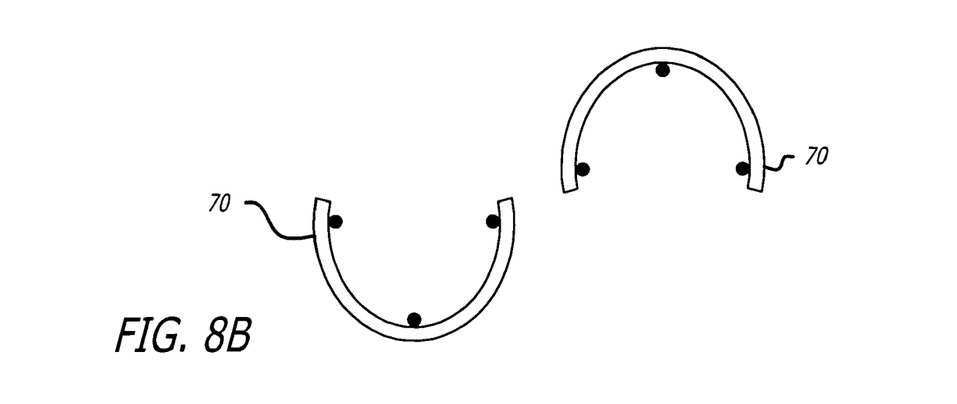
FIG. 8B is a schematic, cross-sectional view of a trunk portion depicting non-overlapping docking sections

It is contemplated that the support 60, 70 provided by the docking sections 22, 24 of the trunk portion 12 may be offset, as shown schematically in FIGS. 6B and 8B. Offsetting the docking sections 22, 24 minimizes the amount of material in any given cross-section and further facilitates packing the trunk portion 12 for delivery.

In another embodiment of the invention, the diameter of the trunk portion 12 docking sections 22, 24 and the limb portion 14 docking section 40 are standardized such that each trunk portion 12 docking section 22, 24 is undersized the same amount to be slightly less than the standard limb portion 14 docking section 40. This facilitates an adjustable length implant that can be assembled from a collection of trunk portions 12 and limb portions 14 having various non-standard diameters at the non-docking ends (proximal end 20 for trunk portion 12 and distal end 48 for limb portions 14). The mechanical seal between any trunk portion 12/limb portion 14 combination will be the same regardless of the relative diameters of the aorta and iliac arteries. A physician can ensure a better fit for the graft implant 10 by selecting the desired non-docking end diameters of the trunk portion 12 and limb portions 14, thereby providing maximum flexibility to optimize the graft 10 to a patient's anatomy with a relatively small number of different parts.

It is contemplated that trunk portions 12 with proximal end 20 diameters between 20 and 34 millimeters can be provided with the standardized docking section 22, 24 diameter. It is further contemplated that limb portions 14 with proximal end 48 diameters between 8 and 16 millimeters may be provided with the standardized docking section 40 diameter.

Figure 9:
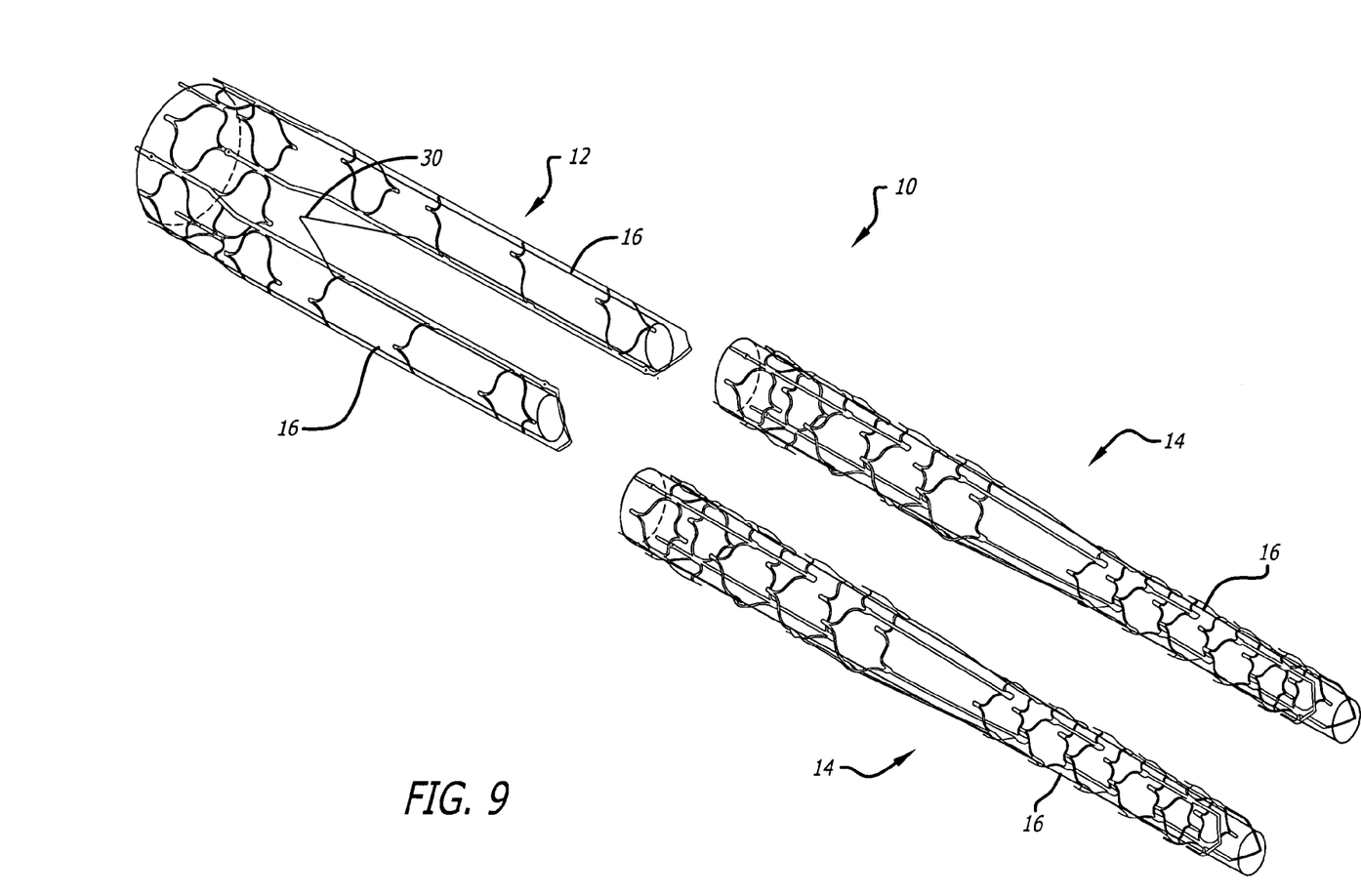
FIG. 9 is a perspective view of an alternate embodiment of a bifurcated stent-graft of the present invention.

Certain embodiments of the present invention may be utilized with various combinations of stent structures and graft material in order to obtain the desired seal between the limb portion 14 and trunk portion 12 and between the trunk portion 12 and the vessel wall. For instance, the stent structure of the trunk portion 12 may be external the graft material 16 with the stent structure of the limb portions 14 internal the graft material 16 for a graft-to-graft seal between trunk portion 12 and limb portion 14. Alternately, the stent structure of the trunk portion 12 may be internal the graft material 16 with the stent structure of the limb portion external the graft material 16 for a stent-to-stent seal between the trunk portion 12 and limb portion 14. Furthermore, the stent structures of the trunk portion 12 and limb portion 14 may both be external or internal the graft material 16 for a stent-to-graft seal between the trunk portion 12 and limb portion 14. (See for example, FIG. 9) Moreover, the graft material 16 may be folded over the distal end of the docking section 22, 24 of the trunk portion 12 in order to facilitate the desired seal between both the trunk portion 12 and limb portion 14 and the trunk portion 12 and vessel wall.

Although the docking sections 22, 24 of the trunk portion 12 and the docking section 40 of the limb portions 14 are shown in the referenced figures as cylindrical, it is contemplated that the invention may be utilized with the various shapes know within the art of endoluminal implants, for instance, tapered or "D" shapes.

While several particular forms of the invention have been illustrated and described, it will be apparent that various modifications can be made without departing from the spirit and scope of the invention. Accordingly, it is not intended that the invention be limited, except by the appended claims.

What is claimed is:

1. A bifurcated graft for repairing vasculature capable of being assembled in-situ, comprising:
   a trunk portion having a graft component with a proximal end and a distal end, the graft component supported by a self-expanding stent structure comprising at least one longitudinal strut that provides longitudinal support substantially the length from the proximal end to the distal end and a plurality of said stent structure extending circumferentially less than 360° around the circumference of the distal end;
   at least one limb portion, each limb portion having a graft component with a proximal end and a distal end, the graft component supported by a self-expanding stent structure comprising at least one longitudinal strut that provides longitudinal support substantially the length from the proximal end to the distal end and a plurality of stent cells along the longitudinal strut that provides at least partial radial support at the proximal and distal ends;
   wherein the graft is assembled by inserting each limb portion proximal end into the trunk portion distal end such that the limb portion proximal end and trunk portion distal end overlap a variable distance between a minimum and maximum amount.

2. The bifurcated graft of claim 1, comprising at least two limb portions.

3. The graft of claim 1, wherein the minimum amount is 10 millimeters.

4. The graft of claim 1, wherein the difference between the minimum amount and maximum amount is 60 millimeters.

5. The graft of claim 1, wherein the trunk portion stent structure further comprises sealing stent cells at the proximal end.

6. The graft of claim 5, wherein the sealing stent cells comprise a number of full cells extending circumferentially 360° around the proximal end.

7. The graft of claim 6, wherein there is an even number of full cells.

8. The graft of claim 1, wherein each limb portion stent structure further comprises sealing stent cells at the distal end.

9. The graft of claim 8, wherein the sealing stent cells comprise a number of full cells extending circumferentially 360° around the distal end.

10. The graft of claim 9, wherein there is an even number of full cells.

11. The graft of claim 1, wherein the trunk portion comprises two or more rows of stent cells extending longitudinally at the distal end.

12. The graft of claim 11, wherein the longitudinal rows comprise full stent cells.

13. The graft of claim 11, wherein the longitudinal rows comprise half stent cells.

14. The graft of claim 11, wherein the longitudinal rows comprise quarter stent cells.

15. The graft of claim 11, wherein the longitudinal rows of stent cells lie in different planes.

16. The graft of claim 11, wherein the stent cells extend circumferentially less than 360° around the circumference of the distal end.

17. The graft of claim 11, wherein the stent cells comprise a number of full cells extending 360° around the circumference of the distal end.

18. The graft of claim 17, wherein there is an even number of full cells.

19. The graft of claim 1, wherein each limb portion stent structure further comprises one or more rows of stent cells extending longitudinally at the proximal end.

20. The graft of claim 19, wherein the longitudinal rows comprise full stent cells.

21. The graft of claim 19, wherein the longitudinal rows comprise half stent cells.

22. The graft of claim 19, wherein the longitudinal rows comprise quarter stent cells.

23. The graft of claim 19 wherein the stent cells extend less than 360° about the circumference of the proximal end.

24. The graft of claim 19 wherein the longitudinal rows comprise a number of full cells extending 360° around the proximal end.

25. The graft of claim 24, wherein there is an even number of full cells.

26. The graft of claim 1, wherein each limb portion stent structure further comprises one or more rows of stent cells extending longitudinally between the proximal and distal ends.

27. The graft of claim 26 wherein the longitudinal rows comprise full stent cells.

28. The graft of claim 26 wherein the longitudinal rows comprise half stent cells.

29. The graft of claim 26 wherein the longitudinal rows comprise quarter stent cells.

30. The graft of claim 26 wherein the stent cells extend less than 360° about the circumference of the stent structure.

31. The graft of claim 26 wherein the longitudinal rows comprise a number of full cells extending 360° around the stent structure.

32. The graft of claim 31, wherein there is an even number of full cells.

33. The graft of claim 1, wherein the graft component of the trunk portion is internal the stent structure.

34. The graft of claim 1, wherein the graft component of the trunk portion is external the stent structure.

35. The graft of claim 1, wherein the graft component of each limb portion is external the stent structure.

36. The graft of claim 1, wherein the graft component of each limb portion is internal the stent structure.

37. The graft of claim 1, wherein the fully expanded diameter of the trunk portion distal end is less than the fully expanded diameter of the limb portion proximal end.

* * * * *